United States Patent [19]

Pines

[11] 3,983,108

[45] Sept. 28, 1976

[54] ANTIBIOTIC PURIFICATION PROCESS
[75] Inventor: Seemon Pines, Murray Hill, N.J.
[73] Assignee: Merck & Co., Inc., Rahway, N.J.
[22] Filed: Feb. 10, 1975
[21] Appl. No.: 548,466

[52] U.S. Cl................................ 260/243 C; 424/250
[51] Int. Cl.² ................ C07D 501/24; C07D 501/60
[58] Field of Search ................................ 260/243 C

[56] References Cited
UNITED STATES PATENTS

| | | | |
|---|---|---|---|
| 3,467,654 | 9/1969 | McCormick | 260/243 C |
| 3,709,880 | 1/1973 | Goegelman et al. | 260/243 C |
| 3,733,320 | 5/1973 | Pines et al. | 260/243 C |

*Primary Examiner*—Nicholas S. Rizzo
*Assistant Examiner*—Jose Tovar
*Attorney, Agent, or Firm*—James A. Arno; Donald J. Perrella

[57] ABSTRACT

Cephamycin C is concentrated and purified by subjecting a fermentation broth which contains Cephamycin C to the following sequence of steps: filtration at acidic pH, adsorption of filtrate on activated carbon, removing the adsorbed antibiotic by contacting the carbon with a mixture of water and a polar organic solvent, contacting the eluate with an anion exchange resin, and eluting the resin with a salt solution at a pH of from about 5.5 to about 10.

10 Claims, No Drawings

ANTIBIOTIC PURIFICATION PROCESS

BACKGROUND OF THE INVENTION

The present invention relates to the concentration and purification of Cephamycin C. More particularly it relates to the concentration and purification of Cephamycin C from a fermentation broth which contains Cephamycin C.

Cephamycin C is a cephalosporin antibiotic having the structural formula

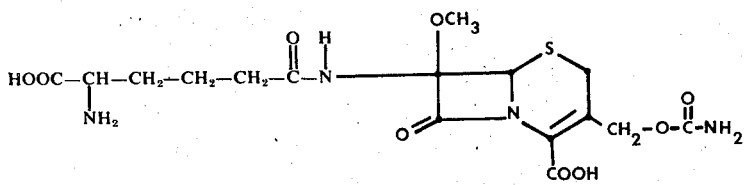

The preparation of this antibiotic by a fermentation process is reported by Stapley et al., Antimicrobial Agents and Chemotherapy, September 1972, pp. 122–131. In such a process it is necessary to separate the desired product from large volumes of liquid containing large amounts of undesired materials. Such separation is time consuming and expensive.

It is accordingly, an object of the present invention to provide an improved method for obtaining Cephamycin C from a fermentation broth. Another object is to provide a method for concentrating and purifying Cephamycin C from a fermentation broth in which it has been prepared. A further object is to provide a simple and economical process for concentrating and purifying Cephamycin C from a fermentation broth. These and other objects of the present invention will be apparent from the following description.

SUMMARY OF THE INVENTION

Cephamycin C is concentrated and purified by subjecting a fermentation broth which contains Cephamycin C to the following sequence of steps: filtration at acidic pH, adsorption of filtrate on activated carbon, removing the adsorbed antibiotic by contacting the carbon with a mixture of water and a polar organic solvent, contacting the eluate with an anion exchange resin, and eluting the resin with a salt solution at a pH of from about 5.5 to about 10.

DETAILED DESCRIPTION

Cephamycin C is prepared according to the fermentation process described by Stapley et al. supra. At the end of the fermentation of Cephamycin C is present in a large volume of liquid which contains large amounts of undesired organic and inorganic materials. According to the present invention, the Cephamycin C present in such a fermentation broth is concentrated and purified by a sequence of operations involving acidification, filtration, adsorption on carbon, optionally washing the carbon adsorbate with water and then eluting with a mixture of water and a polar organic solvent, contacting the eluate with an anion exchange resin, and eluting the resin at a pH of from about 5.5 to about 10. The steps of the present process will now be described in detail.

A. The fermentation broth is acidified to a pH of from about 2.5 to about 4.5, preferably to a pH of about 3.5 by the addition of acid, preferably a mineral acid for reasons of economy, and most preferably, $H_2SO_4$. The acidified broth is then filtered, preferably after adding a filter aid such as, for example, diatomaceous earth.

B. The filtrate is contacted with activated carbon which, optionally but preferably, has been pretreated with a mineral acid and then washed with water so that the alkalinity of the ash is substantially removed, preferably by being adsorbed on a carbon column wherein the carbon has high porosity and relatively large pore size as well as good physical strength such that the carbon particles at the bottom of the column are not crushed by the weight of the carbon particles in the upper portion of the column. The carbon particles preferably are of such a size that they will pass through a Tyler 12 mesh screen and be retained on a Tyler 40 mesh screen. A suitable carbon is Pittsburgh CAL carbon. The adsorption takes place during a pseudo contact time of from about 15 minutes to about 90 minutes (residence time of filtrate in the column).

C. The activated carbon containing adsorbed antibiotic is then optionally but preferably, washed with a quantity of water sufficient to displace undesired materials while having essentially no effect on adsorbed Cephamycin C.

D. The carbon containing adsorbed Cephamycin C is next contacted with a quantity of a mixture of water and a polar organic solvent sufficient to desorb the Cephamycin C. The polar organic solvent may be, for example, a ketone, an alcohol, or an ester. Preferred mixtures are a 1:1 (vol/vol) mixture of acetone and water, water saturated with butanol, or a saturated mixture of ethyl acetate in water.

E. The mixture of water and the polar organic solvent containing the desorbed Cephamycin C is then treated with an anion exchange resin which retains the Cephamycin C on the column while permitting the water-solvent mixture and impurities to pass through. In general, while any anion exchange resin is operative, not all anion exchange resins are equally effective. Weakly basic anion exchange resins are preferred. Examples of suitable resins are IRA 45, IRA 47, IRA 68 and IRA 93 manufactured by Rohm and Haas Company.

F. The anion-exchange resin is then eluted with a salt having a pH of from about 5.5 to about 10, preferably a pH above 7. Suitable salts are $Na_3PO_4$, $Na_2HPO_4$, NaCl or $NaHCO_3$. The Cephamycin C in the eluant is enriched from about 20 times to about 70 times with respect to accompanying impurities in the starting broth. From about 45% to about 65% of the organic material in the eluant is Cephamycin C.

The following examples illustrate the present invention without, however, limiting the same thereto.

EXAMPLE 1

To 568 liters of fermentation broth containing Cephamycin C prepared as described in U.S. Pat. No. 3,770,590 there is added a quantity of 3N-sulfuric acid sufficient to adjust the pH to 3.5 followed by 1.54 kg. of diatomaceous earth (Hyflo Super-Cel). The acidified broth is then filtered on a drum filter and the filtrate is fed to a column of activated carbon (Pittsburgh CAL) having a bed volume of 44.3 liters of carbon and passed through the carbon bed at such a rate that the residence time in the column is about 30 minutes.

The carbon containing the absorbed Cephamycin C is then washed with about two bed volumes of water to displace from the column undesired materials remaining with the residual filtrate.

The carbon column is next contacted with 4.5 bed volumes of a 1:1 (vol/vol) mixture of acetone and water. The first 0.5 bed volume of effluent is discarded and the remaining effluent containing desorbed Cephamycin C is passed through a column containing 44.3 liters of IRA 68 anion exchange resin.

The resin is then eluted with a 0.5 M solution of $Na_3PO_4$. The first 15 liters of eluant are discarded and the succeeding 225 liters are collected for further processing. About 52% of the organic material in this portion of the eluant consists of Cephamycin C whereas in the starting fermentation broth only about 3% of the organic materials consists of Cephamycin C. The amount of Cephamycin C measured in the eluant is 62% of the amount present in the original broth.

EXAMPLE 2

The procedure of Example 1 is repeated except that in this case the activated carbon has been subjected to an acid pretreatment.

The acid pretreatment of the carbon consists in passing 1 bed volume of 1N-sulfuric acid through the column at a temperature above 50°C. The column is then washed upflow with water at a temperature above 50°C. and then washed with unheated water until the pH of the effluent is greater than 4.0. About 58% of the organic material in that portion of the eluant from the anion exchange resin which is collected consists of Cephamycin C whereas in the starting fermentation broth only about 3% of the organic material consists of Cephamycin C. The amount of Cephamycin C measured in the eluant is 71% of the amount present in the original broth.

What is claimed is:

1. A process for separating Cephamycin C from fermentation broth impurities which comprises filtering a fermentation broth containing Cephamycin C at a pH of from about 2.5 to about 4.5, adsorbing the filtrate on activated carbon, removing the adsorbed Cephamycin C from the carbon by contacting the carbon with a mixture of water and a polar organic solvent, contacting the desorbed filtrate with an anion exchange resin, and eluting the resin with a salt solution at a pH of from about 5.5 to about 10.

2. A process according to claim 1 wherein the fermentation broth is filtered at a pH of about 3.5.

3. A process according to claim 1 wherein the activated carbon has a particle size less than about 12 mesh and greater than about 40 mesh.

4. A process according to claim 1 wherein the polar organic solvent is acetone.

5. A process according to claim 1 wherein the anion exchange resin is a weakly basic anion exchange resin.

6. A process according to claim 1 wherein the resin is eluted with $Na_3PO_4$.

7. A process according to claim 1 wherein the resin is eluted at a pH above 7.

8. A process according to claim 1 wherein the Cephamycin C adsorbed on the activated carbon is washed with water before contacting the carbon with a mixture of water and a polar organic solvent.

9. A process according to claim 1 wherein the activated carbon has been pretreated with acid until alkalinity of the ash is substantially removed.

10. A process according to claim 1 which comprises filtering a fermentation broth containing Cephamycin C at a pH of about 3.5, adsorbing the filtrate on acid-pretreated activated carbon of a particle size less than about 12 mesh and greater than about 40 mesh, washing the carbon with water, removing the Cephamycin C from the carbon by contacting the carbon with about a 1:1 (vol/vol) of acetone and water, contacting the desorbed filtrate with a weakly basic anion exchange resin, and eluting the resin with $Na_3PO_4$ at a pH above 7.

* * * * *